(12) United States Patent
Krebs

(10) Patent No.: US 9,476,809 B2
(45) Date of Patent: Oct. 25, 2016

(54) GASSING OR FUMIGATION DEVICE AND SYSTEM

(75) Inventor: Tobias Krebs, Gutach (DE)

(73) Assignee: PIETER VAN WEENEN & CO., GmbH, Waldkirch (DE)

( * ) Notice: Subject to any disclaimer, the term of this patent is extended or adjusted under 35 U.S.C. 154(b) by 747 days.

(21) Appl. No.: 12/527,443

(22) PCT Filed: Feb. 13, 2008

(86) PCT No.: PCT/DE2008/000271
§ 371 (c)(1),
(2), (4) Date: Oct. 29, 2009

(87) PCT Pub. No.: WO2008/101471
PCT Pub. Date: Aug. 28, 2008

(65) Prior Publication Data
US 2010/0093067 A1 Apr. 15, 2010

(30) Foreign Application Priority Data

Feb. 21, 2007 (DE) .................... 20 2007 002 538 U

(51) Int. Cl.
| | |
|---|---|
| *C12M 1/00* | (2006.01) |
| *C12M 3/00* | (2006.01) |
| *G01N 1/28* | (2006.01) |
| *B01F 3/04* | (2006.01) |
| *B01F 5/04* | (2006.01) |
| *G01N 35/00* | (2006.01) |

(52) U.S. Cl.
CPC ............... *G01N 1/28* (2013.01); *B01F 3/0446* (2013.01); *B01F 5/0471* (2013.01); *C12M 23/40* (2013.01); *C12M 29/06* (2013.01); *G01N 2035/00178* (2013.01)

(58) Field of Classification Search
CPC ..... C12M 23/40; C12M 29/06; B01F 3/0446
See application file for complete search history.

(56) References Cited

U.S. PATENT DOCUMENTS 4,493,896 A * 1/1985 La Motte et al. .......... 435/283.1
7,125,522 B2 * 10/2006 Hall .............................. 422/552

(Continued)

FOREIGN PATENT DOCUMENTS

| DE | 19712575 A1 | 10/1998 |
|---|---|---|
| DE | 10329983 A1 | 3/2005 |
| DE | 102006043656 A1 | 3/2008 |

(Continued)

OTHER PUBLICATIONS

English translation of DE 10329983, Hassel, Mar. 31, 2005.*

*Primary Examiner* — Nathan Bowers
(74) *Attorney, Agent, or Firm* — Miller, Matthias & Hull LLP

(57) ABSTRACT

Gassing or fumigation apparatus comprising a one-piece specimen receptacle block including at least two specimen receptacles formed therein and a fluid supply device formed therein for the at least two specimen receptacles, and a gassing or fumigation head for supplying gassing or fumigation medium, which gassing or fumigation head is connected to the specimen receptacle block, comprises a gassing or fumigation medium outlet for each of the at least two specimen receptacles and a device formed therein for conducting gassing medium to the gassing or fumigation medium outlets, and gassing or fumigation system including such a gassing or fumigation apparatus.

14 Claims, 15 Drawing Sheets

(56) References Cited

U.S. PATENT DOCUMENTS 7,871,605 B2 * 1/2011 Hampson et al. ........... 424/93.7
2010/0184199 A1 * 7/2010 Klein et al. ................ 435/286.5

FOREIGN PATENT DOCUMENTS

| WO | 02063027 A1 | 8/2002 |
| WO | 2004076609 A1 | 9/2004 |

* cited by examiner

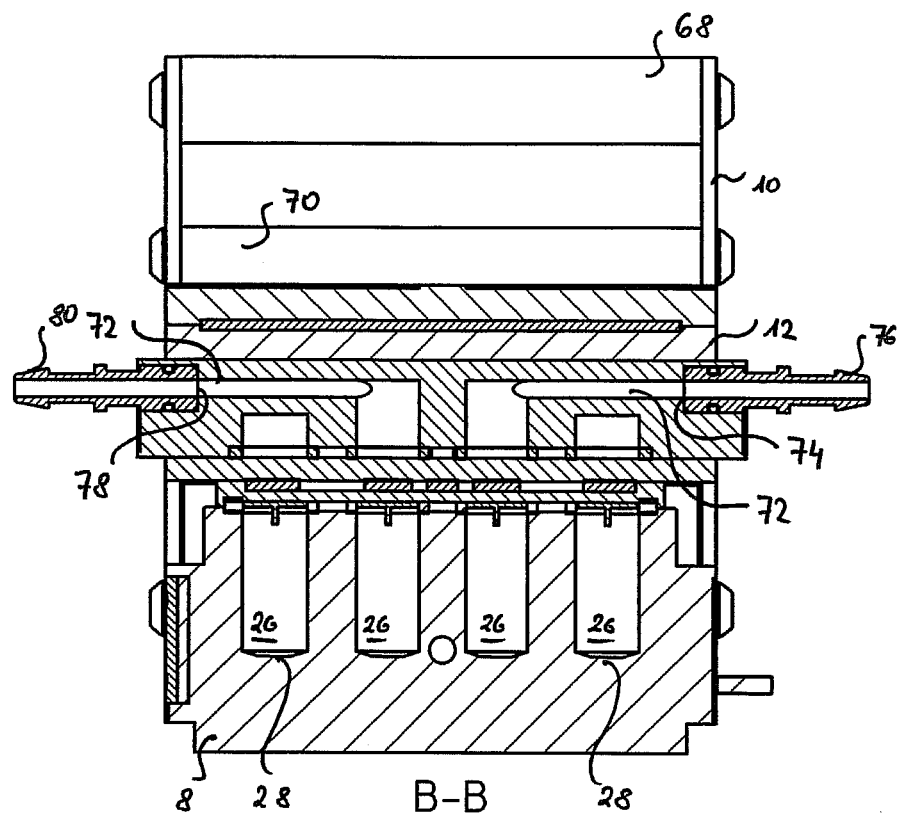
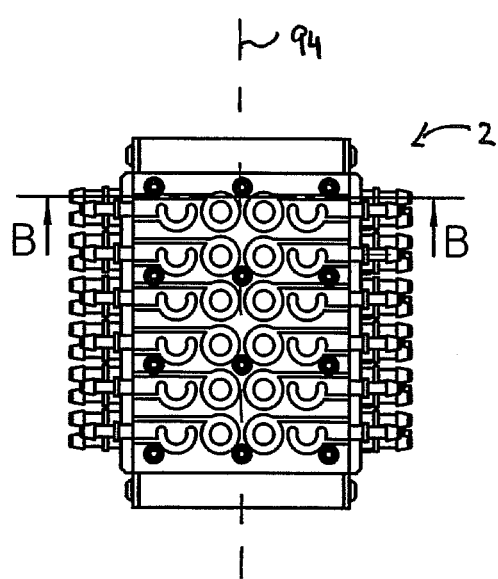
Fig. 2

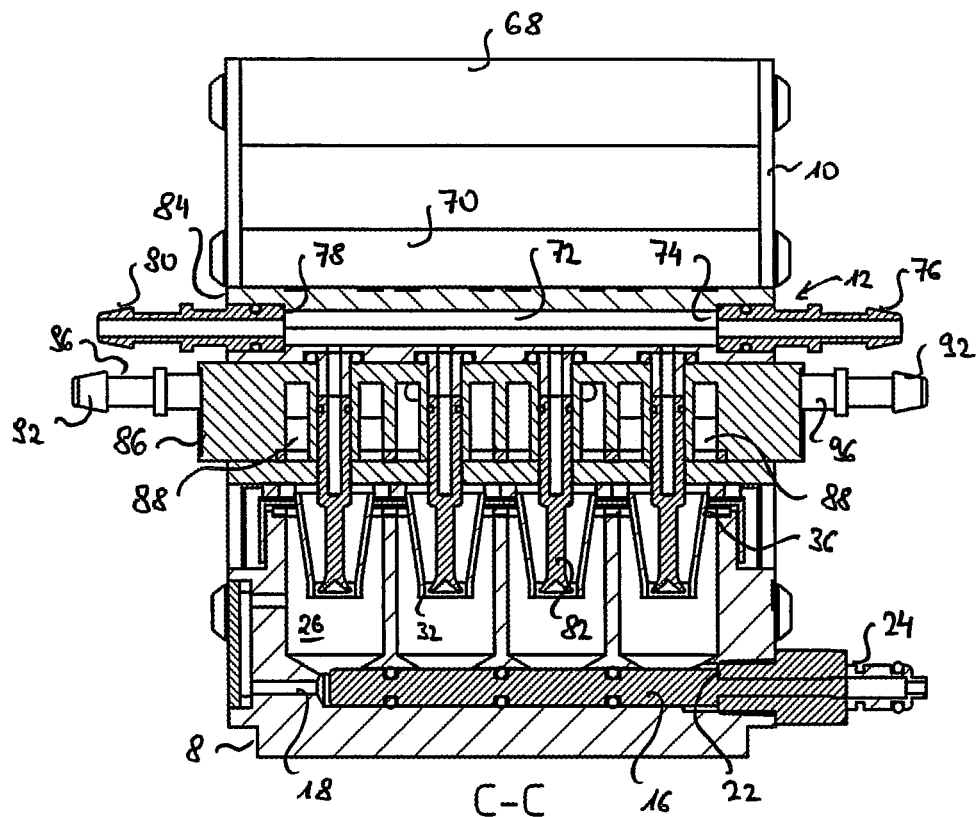
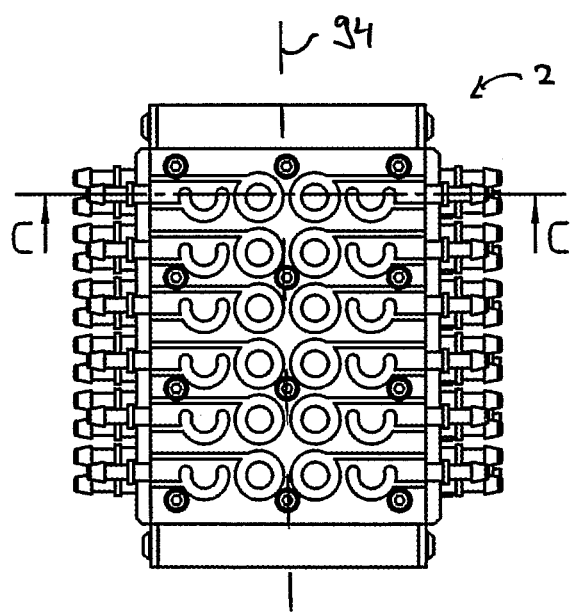
Fig. 3

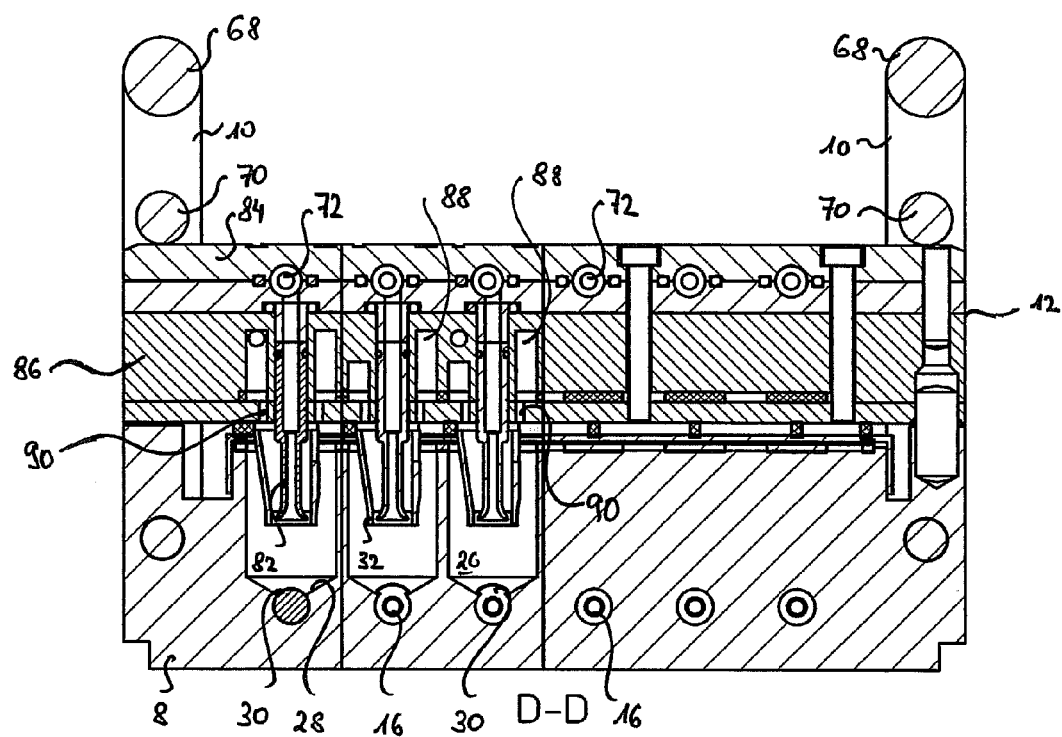
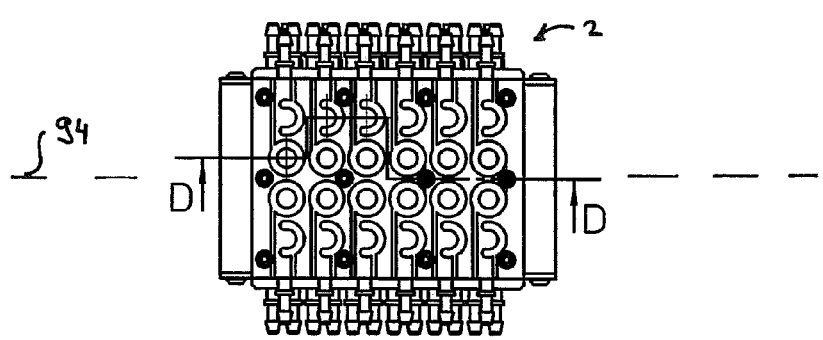
Fig. 4

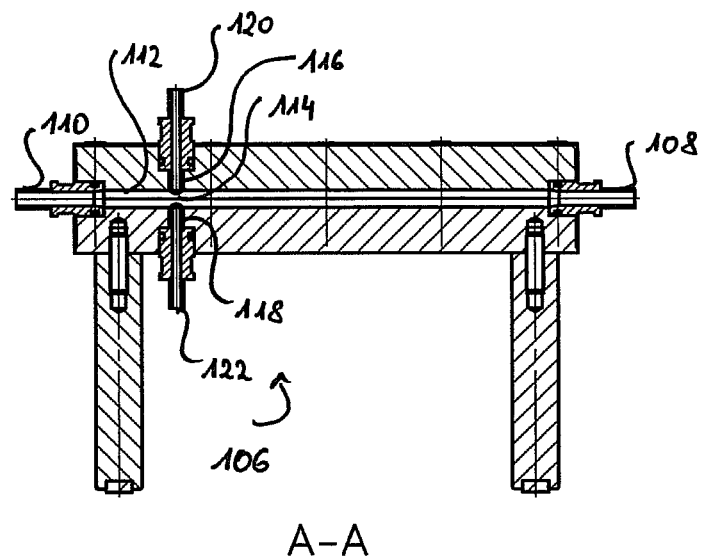
A-A
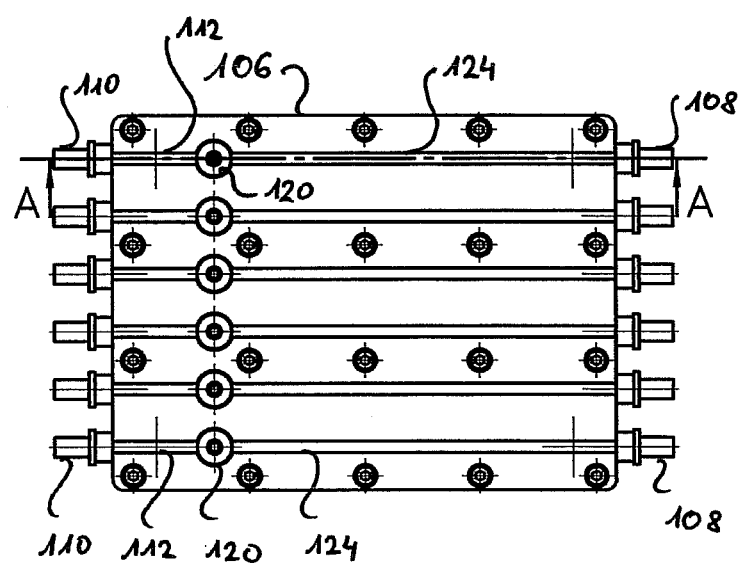
Fig. 13

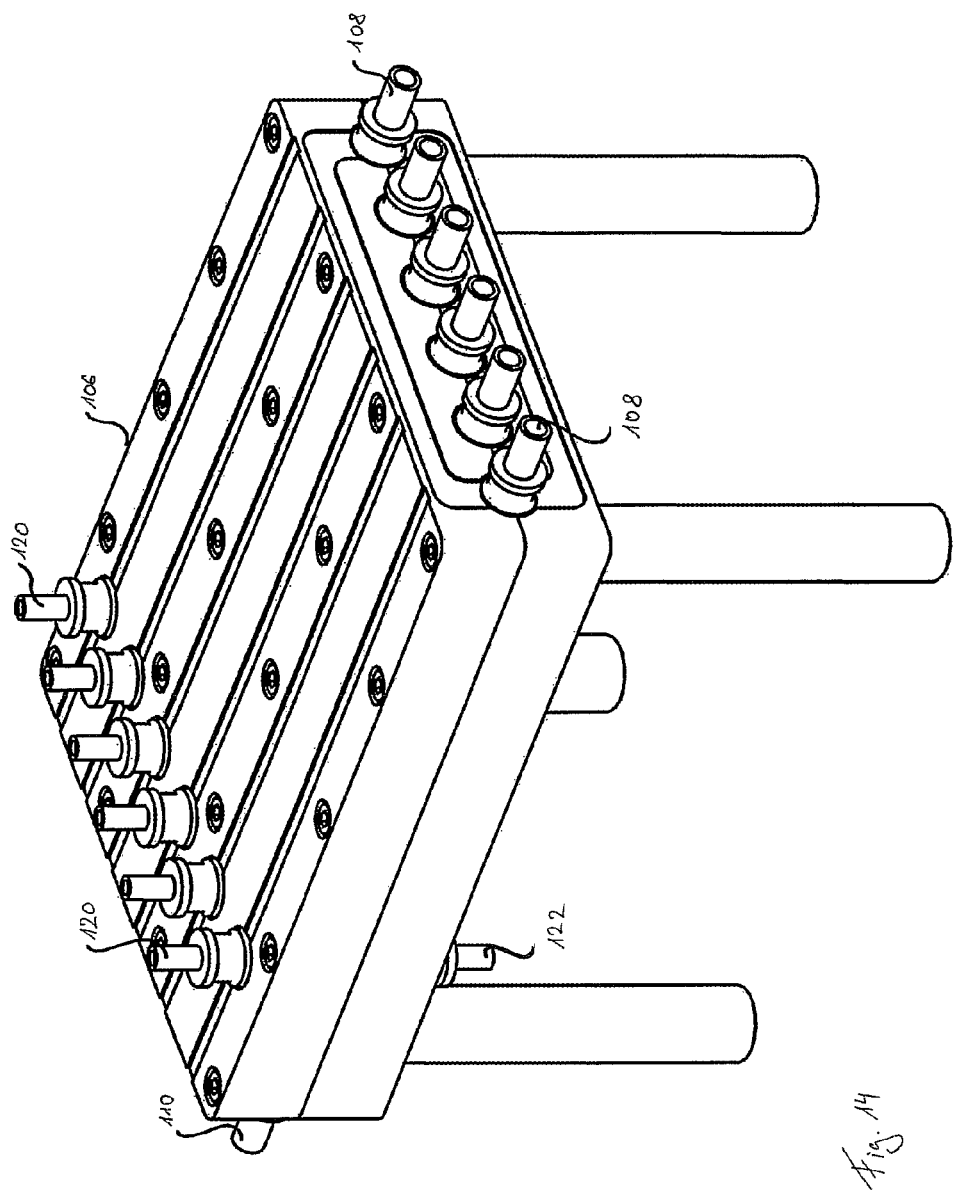

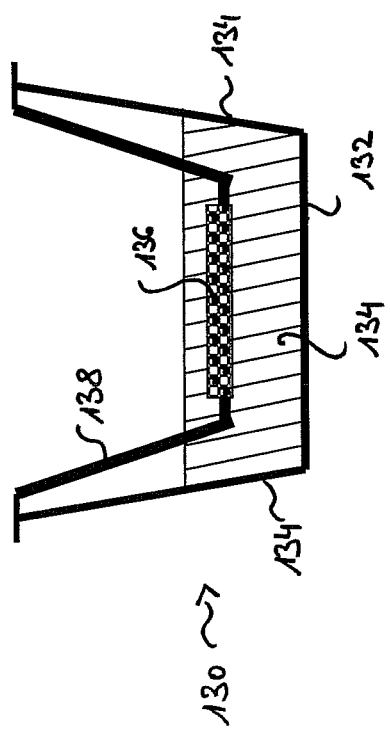

GASSING OR FUMIGATION DEVICE AND SYSTEM

CROSS-REFERENCE TO RELATED APPLICATIONS

This application is a U.S. national stage filing of International Patent Application No. PCT/DE2008/000271 filed on Feb. 13, 2008, which claims priority under the Paris Convention to German Patent Application No. 20 2007 002 538.6, filed on Feb. 21, 2007.

FIELD OF THE DISCLOSURE

This disclosure relates, in general, to fumigation or gassing systems and, in particular, to a fumigation or gassing devices for exposing sample to a gas and a system comprising at least one such fumigation or gassing device.

BACKGROUND OF THE DISCLOSURE

For examining specimens, it is known to gas the same with medium. This is employed, for example, in cell cultures in order to analyze their properties when exposed to one or a plurality of gaseous substances.

The apparatuses usually used for gassing comprise containers in which specimens to be examined are disposed. The specimen containers may be supplied with a medium adapted for gassing the specimens. The gassing medium introduced into the specimen containers contacts the respective specimen.

Known approaches use complex stationary arrangements comprising, in part, numerous sensitive components made of, for example, glass. The manufacture and modification of such arrangements is time, cost and personnel intensive.

There is want of arrangements enabling, for example, gassing of specimens on a large scale and in accordance with industrial quality and cost criteria.

SUMMARY OF THE DISCLOSURE

Systems and devices are disclosed herein that provide compact and variably structured arrangements for gassing or fumigating specimens or otherwise exposing specimens to a gas.

In particular, a gassing or fumigation apparatus is disclosed that comprises comprising a one-piece specimen receptacle block and a gassing head.

The specimen receptacle block comprises at least two integral specimen receptacles formed therein and an integral fluid supply device also formed therein for supplying said receptacles with fluid.

The gassing head is adapted for supplying gassing medium to the specimen receptacles and may, inter alia, be connected to the specimen receptacle block for this purpose. The gassing head comprises a gassing medium outlet for each specimen receptacle and an integral device formed in the gassing head for conducting gassing medium to the gassing medium outlets. The gassing medium conducting device may comprise, for example, one or a plurality of ducts, lines or other components by means of which gassing medium can be transported.

The supply device may be adapted for separate, individual fluid supply of one or a plurality of specimen receptacles.

The device for conducting gassing medium to the specimen receptacles may separately supply individual or a plurality of gassing medium outlets with gassing medium.

The gassing apparatus may comprise an individual level detecting means for at least one specimen receptacle, preferably for all specimen receptacles. By means of the level detecting means, the level of fluid present in a specimen receptacle may be detected.

For supplying individual, a plurality or all specimen receptacles with fluid in an individually controlled manner, a controllable closing member may be used for each corresponding specimen receptacle, which closing member is connected to the central fluid duct and which is capable of controlling supply and/or discharge of fluid from or to said central fluid duct.

For separately supplying individual, a plurality or all specimen receptacles with fluid, at least one separate fluid duct may formed in the specimen receptacle block for each specimen receptacle adapted for this purpose, which fluid duct is connected to a specimen receptacle, for example, via an aperture in the bottom thereof. Fluid ports for supplying and/or discharging fluid, which are connected to separate fluid ducts, may be arranged at the longitudinal sides of the specimen receptacle block.

The level detecting means may comprise a respective individual level meter and/or level indicator for one, a plurality or all specimen receptacles.

In the case of an individual level meter, said meter may be arranged on and/or in a respective inner wall of a corresponding specimen receptacle. Individual level meters may comprise individual or a plurality of sensors, detectors and the like, which are capable of detecting fluid levels in an electric, electronic, optical and/or acoustic manner.

In the case of one or a plurality of individual level indicators, control chambers being in fluid connection with specimen receptacles via through-holes may be used in an outer surface of the specimen receptacle block. In particular, it is contemplated to configure the control chambers and the fluid connection(s) thereof to corresponding specimen receptacles such that a fluid level present in the control chamber is indicative of the fluid level in the associated specimen receptacle.

Individual, a plurality or all control chambers may be provided with a transparent cover for enabling optical control by a user.

Gassing medium ducts extending through the gassing head may be provided for conducting gassing medium to the gassing medium outlets.

The gassing medium ducts may each extend between an inlet port adapted for supplying gassing medium and an outlet port via which gassing medium may be removed.

For individually and separately controlling gassing medium available to individual, a plurality or all gassing medium outlets, the corresponding gassing medium outlets may be connected to the respective gassing medium duct via a controllable closing member.

The gassing head may comprise a separate vacuum chamber for each individual gassing medium outlet. It is further contemplated to use a common vacuum chamber for a plurality or all gassing medium outlets.

In their assembled state, the vacuum chambers are each in communication with a corresponding specimen receptacle via at least one intake opening.

The gassing medium outlets may comprise outlet ends which, for example, have a hollow-cylindrical shape, define frustoconical interior spaces, and comprise a number of outlet ducts each having a polygonal, preferably hexagonal, cross-section and/or a number of outlet ducts each having a circular cross-section.

One or a number of photometers may be arranged in regions, in which individual, a plurality or all gassing medium outlets are supplied with gassing medium.

The specimen receptacle block may comprise a thermally conducting bottom region, which may further be adapted for enabling a positive and/or non-positive operative connection with a base.

The specimen receptacle block and the gassing head may be releasably connected to each other, for example, by means of a clamping mechanism.

The clamping mechanism may comprise one or a number of levers by means of which the specimen receptacle block and the gassing head may be secured to each other. The lever(s) may be rotatably arranged at the specimen receptacle block.

Moreover, the present invention, in particular, provides a gassing system comprising at least one gassing apparatus according to the invention and a base.

The base may comprise a receiving means in which a bottom region of a specimen receptacle block may be arranged.

For thermal control of the at least one gassing apparatus, the base may comprise a heat-emitting device emitting heat, for example, by use of heated fluid and/or electrically heated components.

Further embodiments are defined in the dependent claims and described in the following detailed description of embodiments.

BRIEF DESCRIPTION OF THE DRAWINGS

In the following, preferred embodiments are described with reference to the attached drawings, in which:

FIGS. 1 to 12 show schematic illustrations of embodiments of disclosed gassing or fumigation systems and gassing apparatuses;

FIGS. 13 and 14 show schematic illustrations of a disclosed embodiment of a device for mixing and supplying gassing media; and FIG. 15 shows a schematic illustration of a contemplated specimen receptacle.

For like or comparable components, like reference numerals and terms are used regardless of the respective embodiments.

Figure 1:
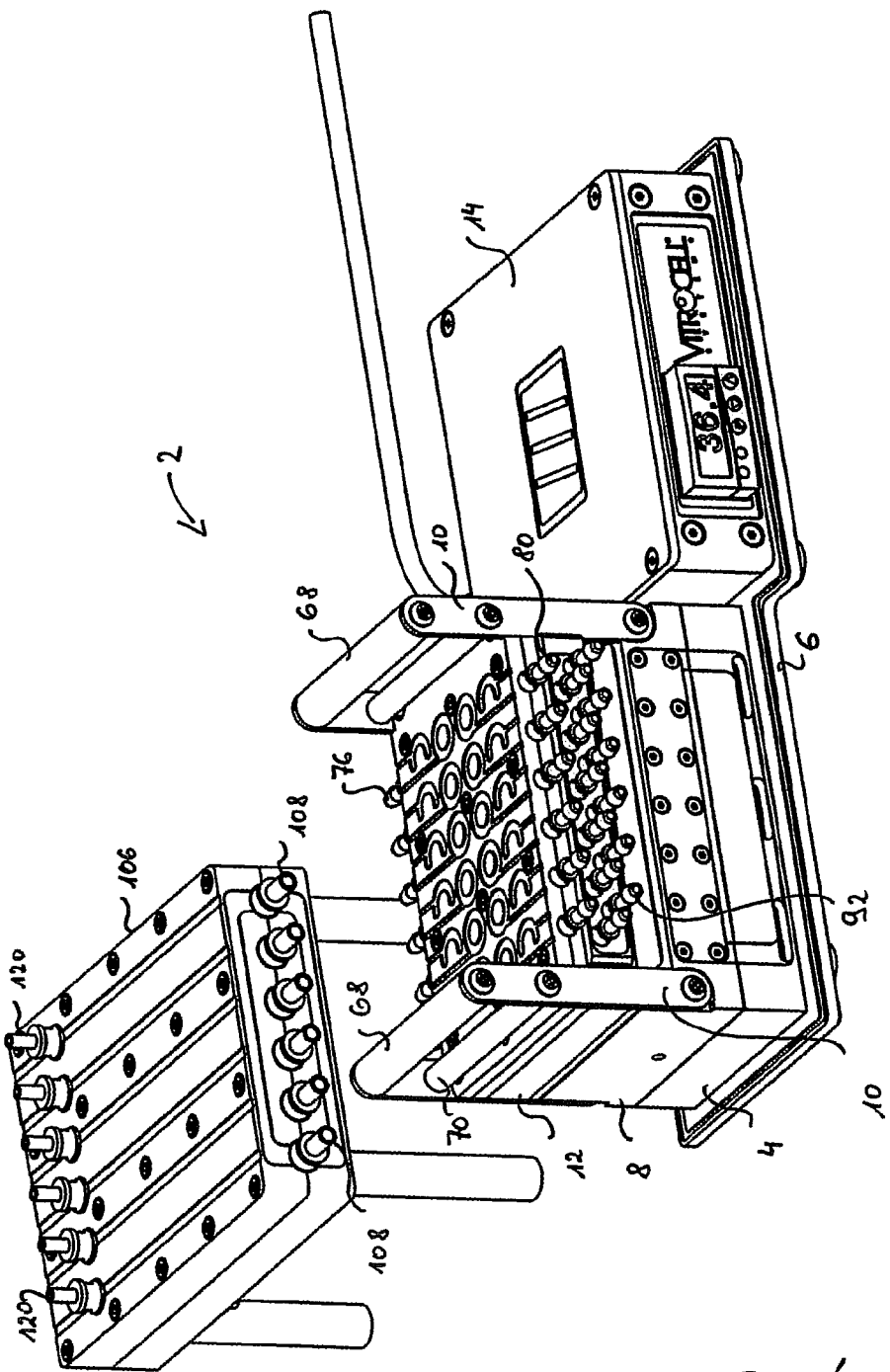

Reference numerals are not repeated in all Figures.

Sealing elements, seals, etc. are indicated by "D" unless specified otherwise.

DETAILED DESCRIPTION OF THE PRESENTLY PREFERRED EMBODIMENTS

Referring to FIGS. 1 to 15, preferred embodiments of a gassing system and preferred embodiments of components which may be used in combination therewith or included therein are described.

The gassing system indicated by 2 as a whole comprises a base 4 which is arranged on a surface 6 (e.g. table surface, base plate, etc.). A specimen receptacle block 8 is arranged on top of the base 4, which specimen receptacle block is releasably connected to a gassing head 12 by means of two levers 10 pivotably arranged on the specimen receptacle block 8. Furthermore, a control means 14 is provided.

The specimen receptacle block 8 and the gassing head 12—together with further components—form a gassing apparatus.

The specimen receptacle block 8 comprises a number of central fluid ducts 16 extending transversely to the longitudinal direction thereof according to the Figures; in not shown embodiments, the fluid ducts 16 extend in the longitudinal direction of the specimen receptacle block 8. According to the illustrations, the fluid ducts 16 are closed at one end 18 each and are connected to a fluid port 24 protruding from the specimen receptacle block 8 at the opposite end 22. The fluid ducts 16 may each be supplied with fluid or fluid may be discharged therefrom via the fluid ports 24.

Alternatively, the ends 18 of the fluid ducts 16 may each be open and connected to a further fluid port (not shown) protruding from the specimen receptacle block 8. This design enables transportation of fluid through the fluid ducts 16 (in both directions).

The specimen receptacle block 8 comprises specimen receptacles 26. The shown embodiments comprise 24 specimen receptacles 26 by way of example. However, other numbers of specimen receptacles 26 may be used, for example, depending on the application. The specimen receptacles 26 are incorporated into the one-piece specimen receptacle block 8, for example, by drilling and/or turning and/or are formed during manufacture of the specimen receptacle block 8. The latter may be performed, for example, by using a corresponding mold, injection or casting mold.

The specimen receptacles 26 each comprise an aperture 30 at their bottoms 28. The apertures 30 are in fluid connection with one of the fluid ducts 16 located below. For this purpose, the apertures 30 may open directly in the respective fluid duct 16, as shown, or may be connected thereto via not shown connectors.

Each fluid duct 16 is connected to a specimen receptacle 26 arranged vertically above it. According to the illustrations, said specimen receptacles are the specimen receptacles 26 which are arranged in line transversely to the longitudinal direction of the specimen receptacle block 8; in not shown embodiments, said specimen receptacles may be specimen receptacles 26 arranged in line in the longitudinal direction.

The fluid ducts 16 serve the purpose of supplying the respective associated specimen receptacles 26 and specimens disposed therein with fluid.

In specimen receptacles 26, specimens (e.g. biological tissue, cell cultures, bacteria cultures, etc.) may be disposed directly, i.e. in particular, without using additional components insertable into the specimen receptacles. Specimens may also be disposed in specimen receptacles 26 using specimen containers 32. Examples of possible specimen containers comprise so-called "cell-culture membrane inserts". For the purpose of arranging specimen containers, individual, a plurality or all specimen receptacles 26 may be formed with a shoulder 34, on which, for example, a bead or ring on an outer circumference of a specimen container may be supported. This will be explained in greater detail with reference to FIG. 15.

In particular, it is contemplated to use an insert 36 comprising a number of specimen containers 32 integrally formed therein, which number may correspond to or may be smaller than the number of specimen receptacles 26. In the latter case, the insert 36 may comprise an opening, in a position where there are no specimen containers, for being able to utilize the specimen receptacles located below, or may be closed whereby the specimen receptacle located below may be covered and/or sealed and/or non-utilizable.

For precisely aligning the insert 36 and the specimen receptacles 26 with respect to each other, tabs 38 may be formed at the lower surface of the insert 36 which are capable of engaging in corresponding recesses (no reference numeral) at the upper open ends of the specimen receptacles 26.

A seal 40 is disposed between the insert 36 and the specimen receptacle block 8, which seal may be made of one piece—as shown—or may comprise a number of individual sealing elements (not shown). According to the illustrations, the seal 40 comprises an upwards raised, circumferential outer rim 42. The rim 42 may, for example, be internally stepped and/or sloped for enabling alignment of the insert 36 and/or use of inserts of various dimensions.

Respective first through-holes 46 extend between the specimen receptacles 26 and a side surface 44 of the specimen receptacle block 8. The first through-holes 46 open into the specimen receptacles 26 in an upper region thereof adjacent to the respective upper specimen receptacle apertures 48 according to the illustrations.

In addition, the specimen receptacles 26 are in fluid connection with the side surface 44 via second through-holes 50. According to the shown embodiments, said fluid connections extend between the side surface 44, the second through-holes 50, the respective fluid duct 16 and the apertures 30 as well as the lower regions of the specimen receptacles 26 according to the illustrations. In not shown embodiments, it is contemplated that the second through-holes 50 open directly into bottom regions of the specimen receptacles 26.

In not shown embodiments, closing members are arranged at or in front of the apertures 30 (or comparable apertures described further below) of individual, a plurality or all specimen receptacles 26. Contemplated closing members comprise flaps, valves etc. having open and closed positions and/or being adapted for opening or closing gradually. The same applies to the closing members mentioned in the following. This enables individual control of the supply and discharge of fluid to or from individual, a plurality or all specimen receptacles 26.

The side surface 44 is provided in a recess 54 formed in an outer surface 52 of the specimen receptacle block 8. A spacing element 56 is fastened in the recess 54, for example, by means of screws, rivets, adhesive connections and the like. The spacing element 56 comprises windows 58, recesses, cut-outs or comparable regions free of material. The windows 58 are each associated with a specimen receptacle 26 in such a manner that the corresponding first and second through-holes 46 and 50 terminate in regions of the side surface 44 left open by the windows 58.

The windows 58 are covered by a transparent cover 60 extending substantially across the entire spacing element 56. Alternatively, separate covering elements arranged above each window 58 may be used.

Each window 58, together with the cover 60 and a corresponding region of the side surface 44, defines a control chamber 62, which is in fluid connection with a corresponding specimen receptacle 26 via the respective first and second through holes 46 and 50. It is contemplated that, except for the first and second through-holes 46 and 50, the control chambers 62 are sealed in a fluid-tight manner; this applies, in particular, to the arrangement of the spacing element 56 and the cover 60, wherein fluid tightness may be achieved, for example, in a non-positive and/or positive manner, as well as by using sealing components in a non-positive and/or positive manner.

The fluid level in the respective control chambers 62 and thus in corresponding specimen receptacles 26 may be controlled visually via the windows 58. The control chambers 62, the windows 58, the first and second through-holes 46 and 50 and the cover 60 are parts of level detecting means for corresponding specimen receptacles 26.

Alternatively or in addition, one or a plurality of measuring sensors may be associated with individual, a plurality or all specimen receptacles 26, by means of which the current fluid levels present therein may be detected. The measuring sensors may be attached to the inner surfaces of specimen receptacles 26 and/or integrated therein. Control and supply lines to measuring sensors may be wireless and/or wired.

For arranging the gassing head 12 in a correct position on the specimen receptacle block 8, individual or a number of guiding means are provided which may also be encoded. The shown embodiments comprise pins 64 extending from the upper surface of the specimen receptacle block 8, which are engaged in guiding apertures 66 in the gassing head 12 during assembly.

Figure 5:
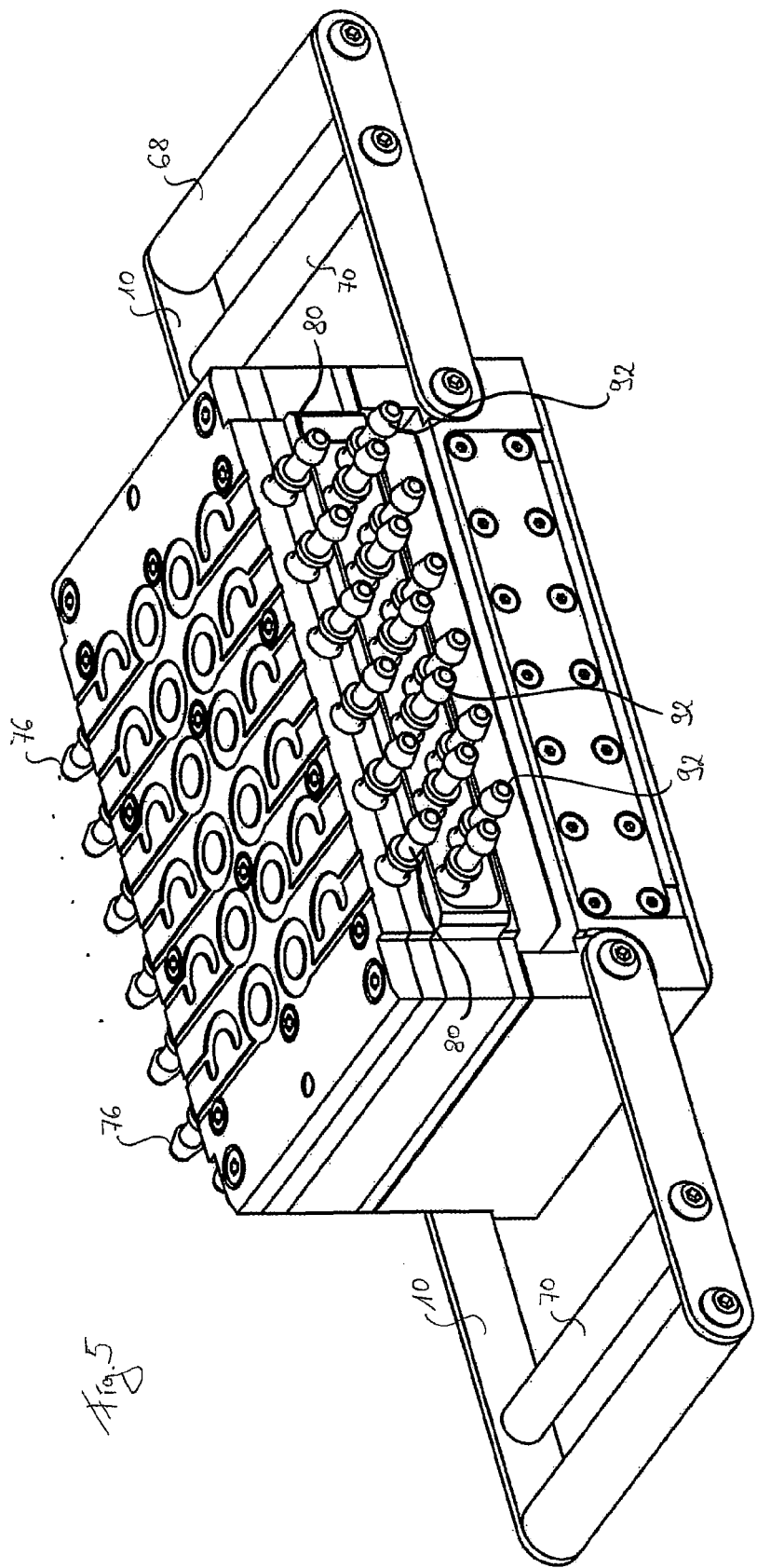
Figure 6:
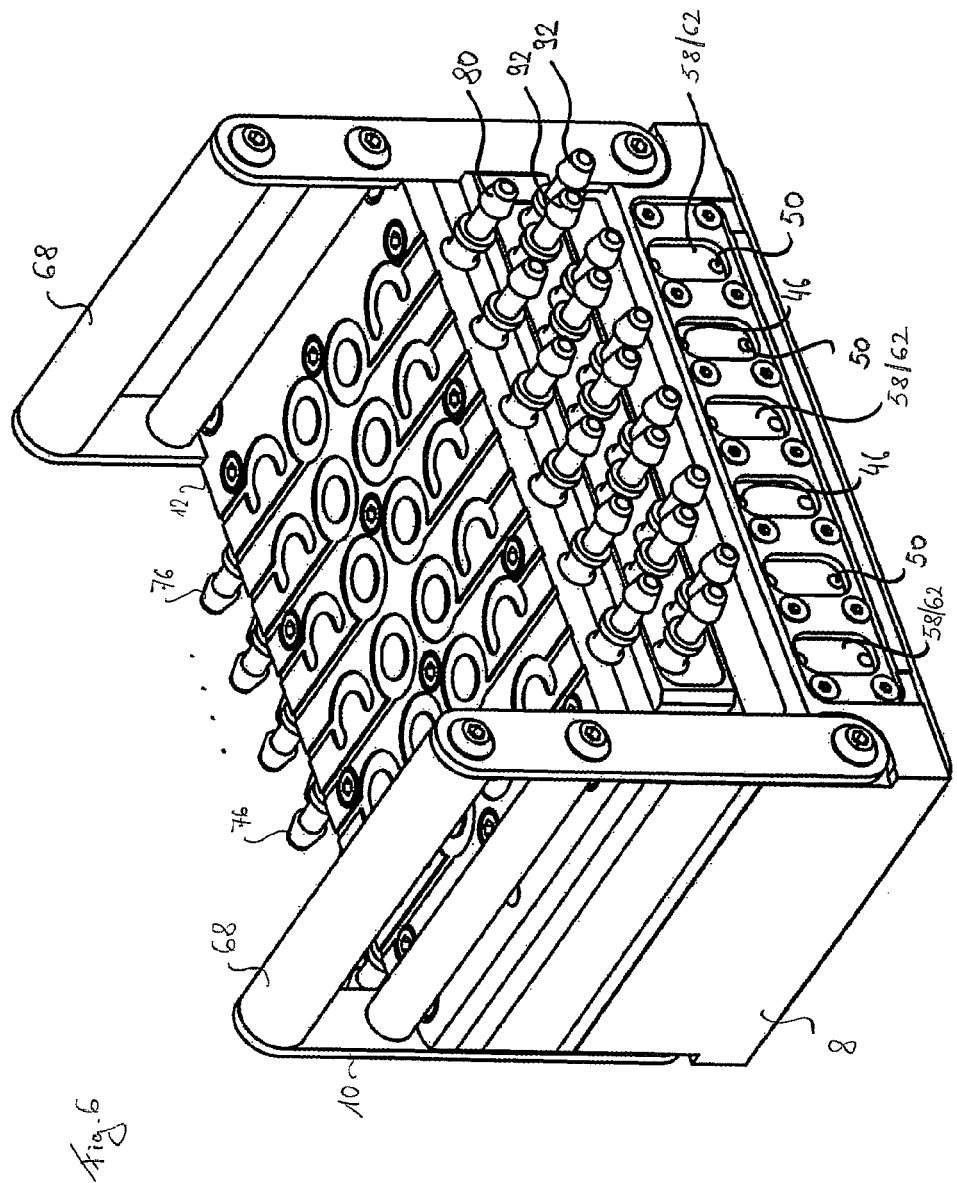
Figure 7:
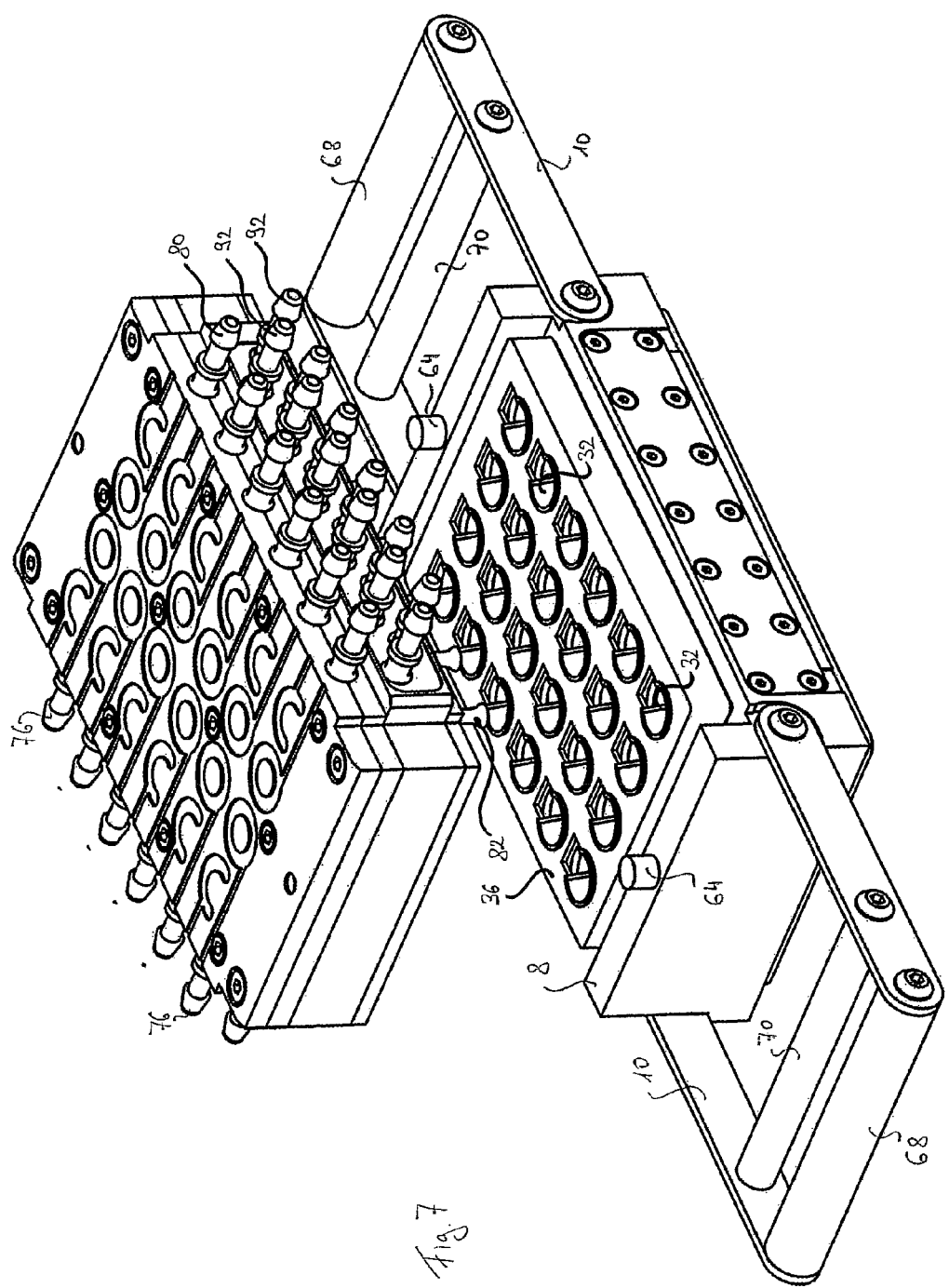
Figure 8:
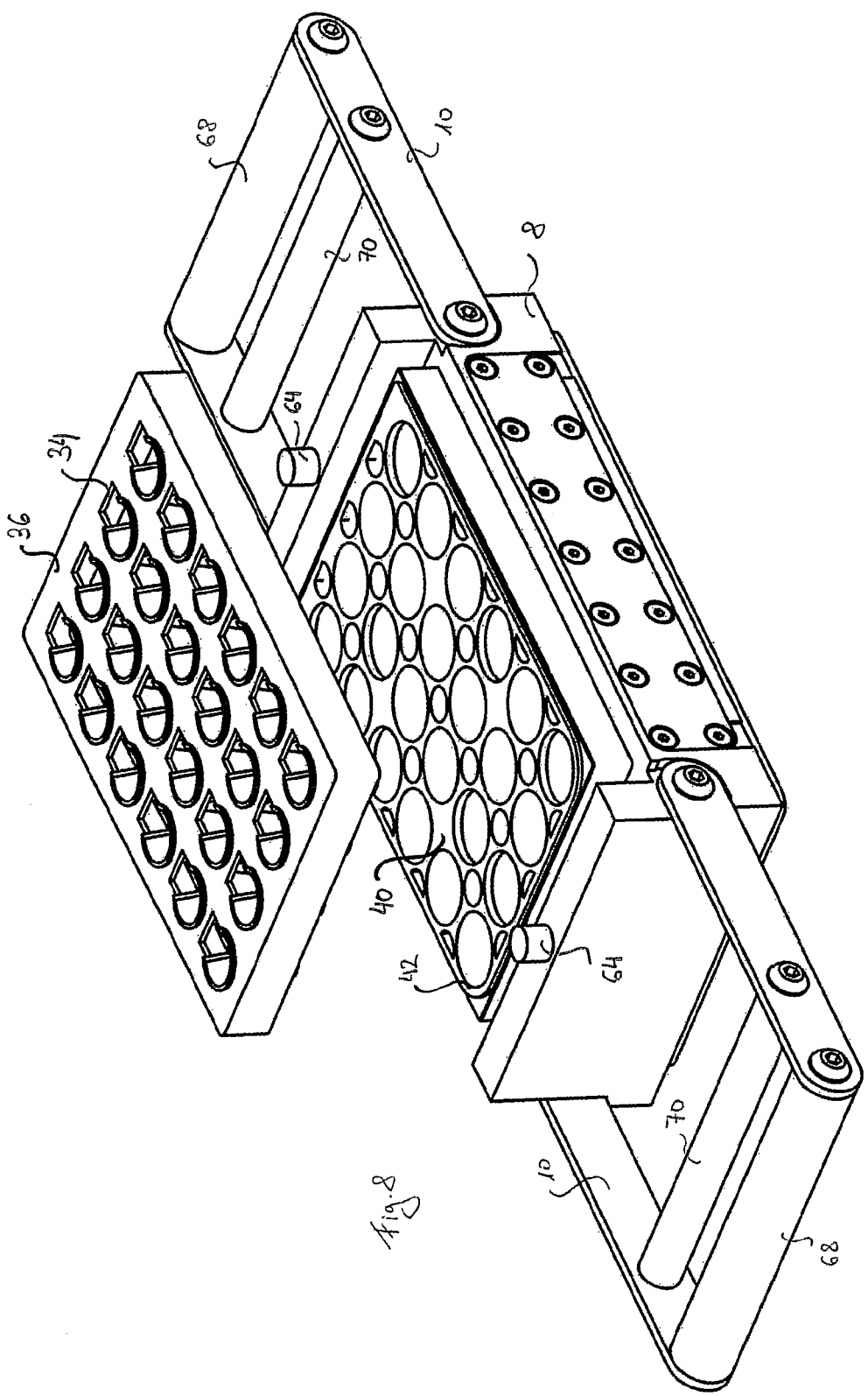
Figure 9:
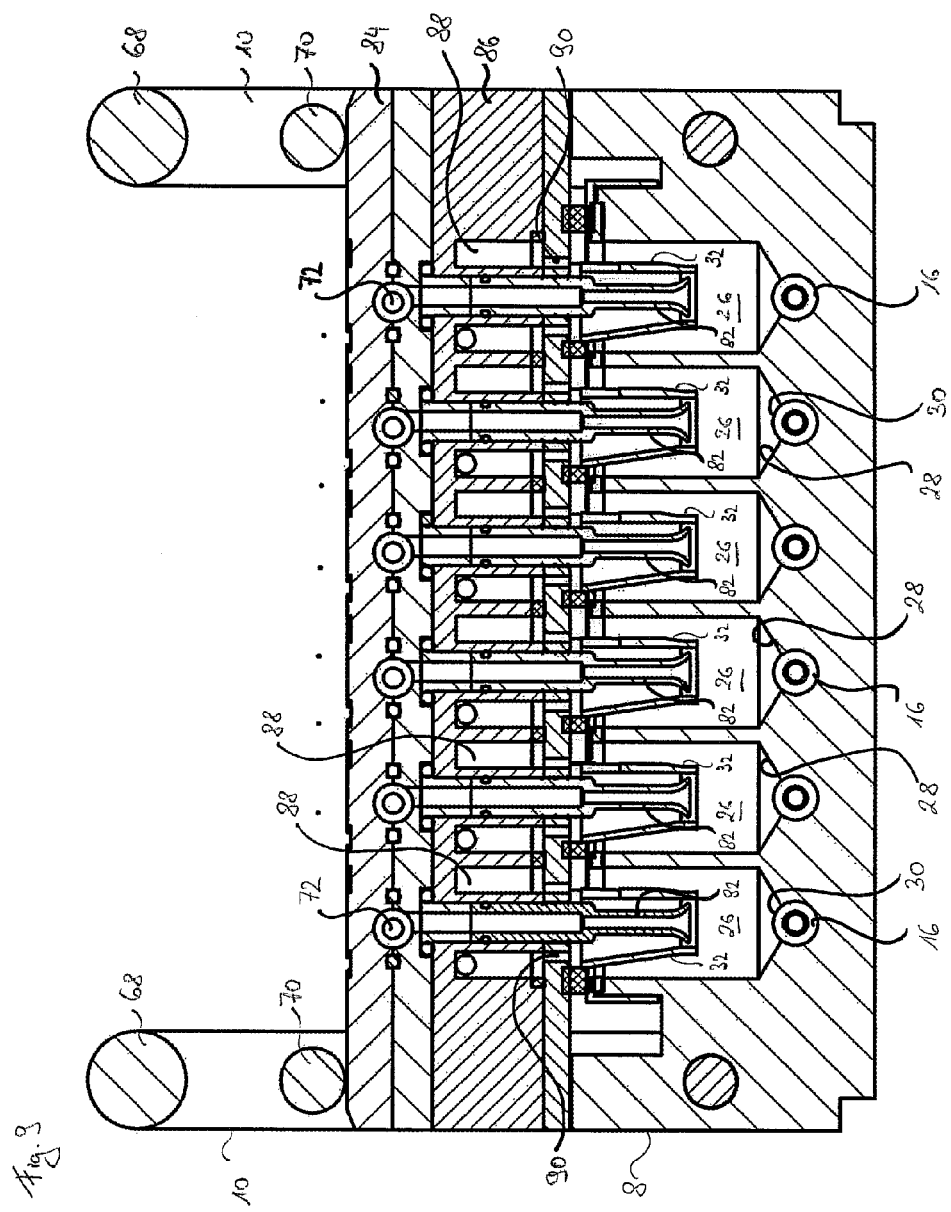
Figure 10:
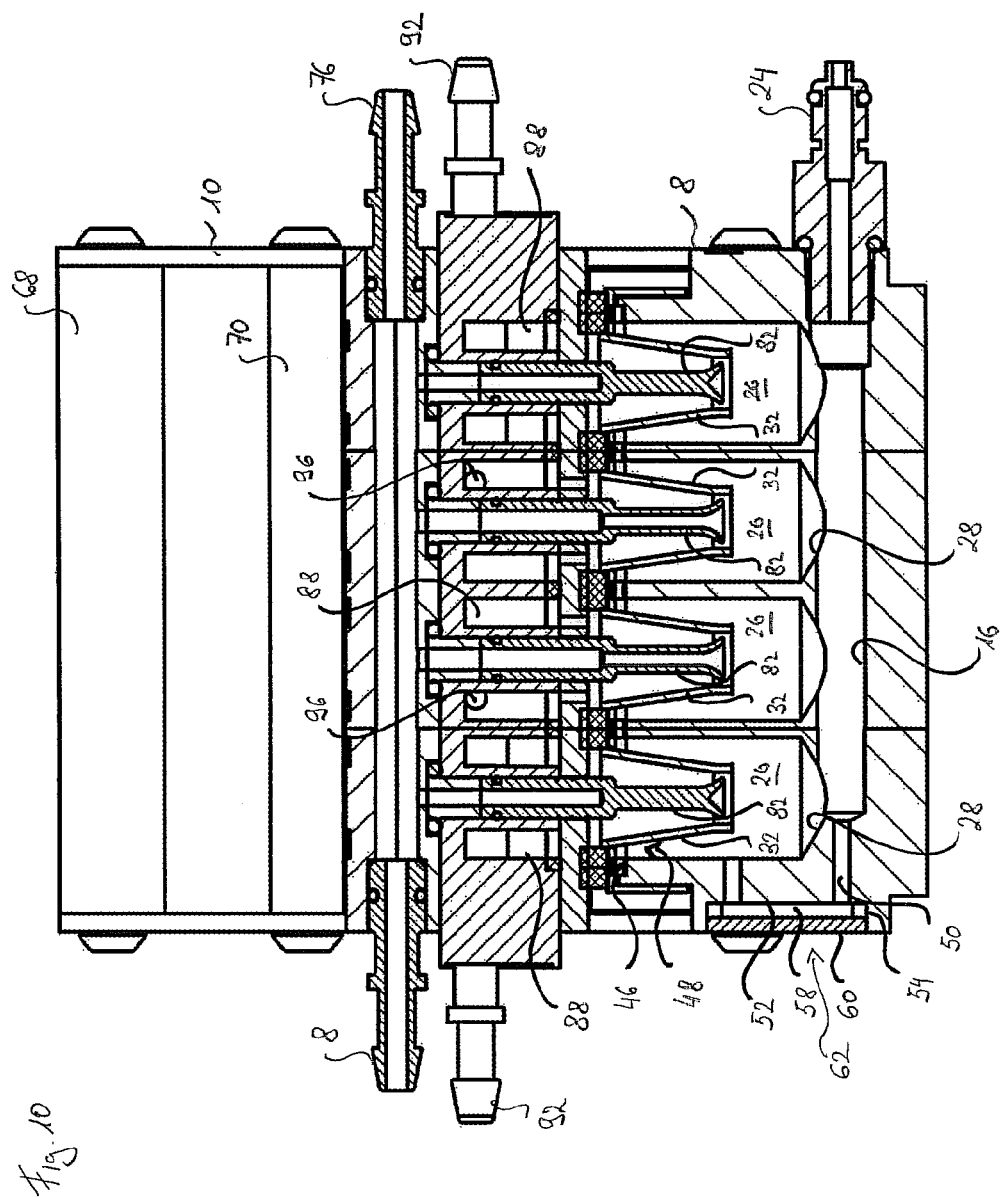
Figure 11:
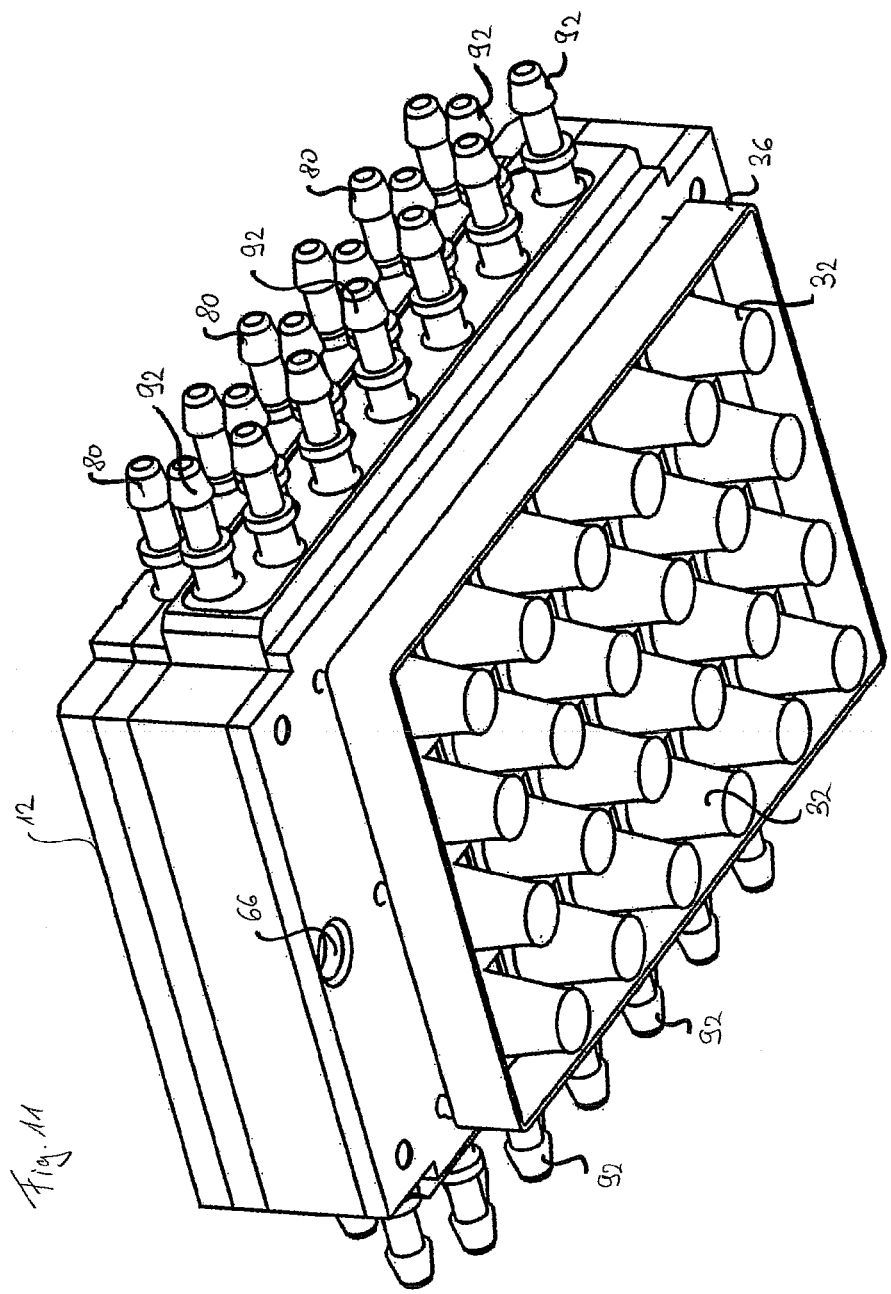
Figure 12:
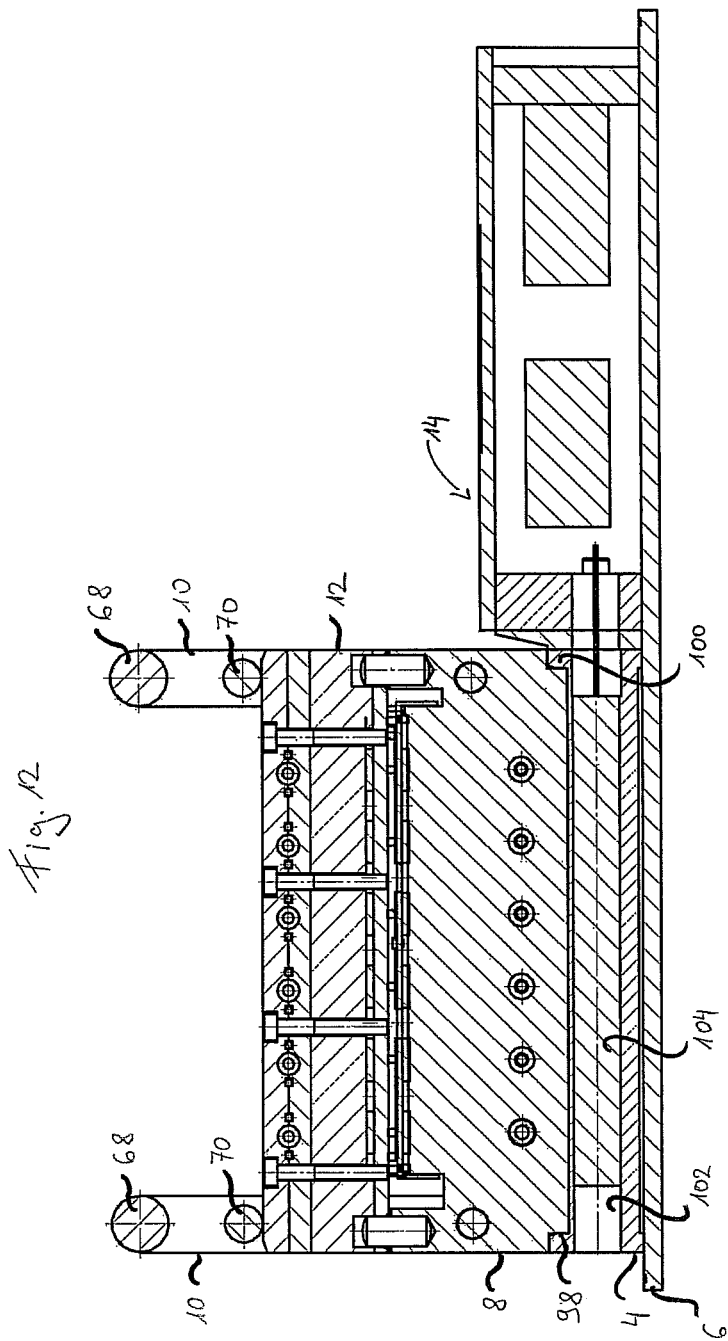

When the gassing head 12 is arranged on the specimen receptacle block 8, as shown for example in FIG. 5, they may be secured to each other by pivoting the levers 10 from the position shown in FIG. 5 into the position shown in FIG. 6. For removing the gassing head 12, the levers 10 are moved into the position shown in FIG. 5.

The levers 10 may comprise handles 68 for actuation thereof. The levers 10 may comprise clamping elements 70 cooperating with upper surfaces (no reference numeral) of the gassing head 12 in the position shown in FIG. 3 and pressing the gassing head against the specimen receptacle block 8. This may at least contribute in achieving fluid-tight connection regions between the gassing head 12 and the specimen receptacle block 8, in particular, in regions of the specimen receptacles 26.

Gassing medium conducting ducts 72 extend through the gassing head 12. The ends 74 of the gassing medium conducting ducts 72 are each connected to an inlet port 76. The opposite ends 78 are each connected to an outlet port 80. The inlet ports 76 are each adapted for supplying gassing medium. Not required and/or excess gassing medium may be removed via the outlet ports 80.

The gassing medium conducting ducts 72 are each associated with the specimen receptacles 26 located below. According to the illustrations, said specimen receptacles are the specimen receptacles which are arranged in line transversely to the longitudinal direction of the specimen receptacle block 8. In not shown embodiments, the gassing medium conducting ducts 72 extend in the longitudinal direction of the specimen receptacle block 8; also in this case, they may be in fluid connection with the respective specimen receptacles 26 located below.

It should be noted that the orientations of the fluid ducts 16 and the gassing medium conducting ducts do not have to coincide, but may extend, e.g. perpendicularly or at a different angle to each other.

The specimen receptacles 26 associated with a gassing medium conducting duct 72 may be supplied with the same gassing medium which may differ from the gassing medium or media supplied to other specimen receptacles 26 via corresponding gassing medium conducting ducts 72.

The gassing head 12 comprises a gassing medium outlet 82 for each specimen receptacle 26. In contrast to the illustrations, the gassing medium outlets 82, in their assembled state, may extend into the respective specimen receptacles 26 to a varying extent. The gassing medium outlets 82 are each connected to the respective gassing medium conducting duct 72.

According to the illustrations, the gassing head 12 comprises an upper part 84, in which the gassing medium conducting ducts 72 are formed. The gassing head 12 comprises a part 86 being located below in its assembled state, in which the gassing medium outlets 82 are arranged. For connecting the gassing medium ducts 72 to the gassing medium outlets 82, outlets (no reference numeral) are arranged at the gassing medium ducts 72. The outlets are connected, in their assembled state, with the upper ends of the corresponding gassing medium outlets 82 according to the illustrations. For sealing said connection regions, a seal may be used which is arranged between the parts 84 and 86. The seal may comprise, for example, individual annular sealing elements or may be a planar seal with apertures.

In not shown embodiments, a one-piece structure may be used at least for the parts 84 and 86, which structure provides integral connections between the gassing medium ducts 72 and the gassing medium outlets 82.

In not shown embodiments, closing members may be arranged in front of individual, a plurality or all gassing medium outlets 82 or may be integrated therein. This enables individual control of the connections between the gassing medium ducts 72 and the gassing medium outlets 82.

In this way, specimen receptacles 26 may be individually, in series, in groups, etc., brought into fluid connection with the respective gassing medium conducting duct 72 and separated therefrom in a controlled manner in order to permit or prevent supply of the gassing medium in a controlled manner. Such embodiments may be used in connection with or without use of embodiments described further below wherein a vacuum may be individually applied to the specimen receptacles for gassing the specimen receptacles 26 or the specimens arranged in an arbitrary configuration.

A vacuum chamber 88 each is associated with the gassing medium outlets 82. The vacuum chambers 88 each comprise at least one aperture 90 opening into the corresponding specimen receptacle 26 and being in fluid connection with the associated gassing medium outlet 82 via said specimen receptacle. Each vacuum chamber 88 may be connected to a vacuum generating device via a vacuum duct 96 of its own and a vacuum port 92 connected therewith and protruding from the specimen receptacle block 8. The vacuum chambers may be supplied with vacuum via a common vacuum generating device or respective separately associated individual vacuum sources. An individual vacuum control of the vacuum chambers 88 may also be achieved by means of closing members (not shown), for example in form of valves, arranged between vacuum source and vacuum chamber.

In the shown embodiments, the specimen receptacles 26 arranged on one side with respect to the central plane 94 are associated with vacuum ducts 96 leading to vacuum ports 92 on the same side. In further embodiments, all vacuum ducts 96 may be led to one side of the specimen receptacle block 8. As shown in the Figures, the vacuum ducts 96, with respect to horizontal, are arranged in different, two in this case, planes and/or offset with respect to each other. This enables a more compact design as compared to an arrangement in one plane. For a compact design, vacuum ducts 96 could be used—in addition or alternatively—not extending in a straight line between vacuum port and vacuum chamber, but extending, at least in part, in a curved line between vacuum chambers and vacuum port.

Individual or a plurality of common vacuum chambers may also be associated with a plurality of specimen receptacles 26, which vacuum chambers comprise at least one aperture to each specimen receptacle 26. Also an individual vacuum chamber for all specimen receptacles 26 is contemplated. In such cases, vacuum could be applied to all specimen receptacles 26 associated with a common vacuum chamber 88. An individual gassing of specimen receptacles 26 may then be achieved, as described above, e.g. via closing members acting on gassing medium outlets 82.

The base 4 comprises a receiving means 98 adapted for arranging the specimen receptacle block 8 therein. For positioning the specimen receptacle block 8 on the base 4, the lower surface of the specimen receptacle block 8 may be formed complementary with the receiving means 98 or the rims 100 defining the same.

The base 4 may be adapted for controlling the temperature of the specimen receptacle block 8. For this purpose, in particular, regions of the base 4 contacting the specimen receptacle block 8 when arranged thereon, may be made of a heat conducting material. In contrast thereto, regions of the base 4 not contacting the specimen receptacle block 8 may be adapted for avoiding undesired heat loss and heat dissipation to the environment, for example, by means of a corresponding choice of material and/or coatings and/or integrated structures. In an embodiment not shown here, the base 4 may comprise one or a plurality of ducts which may be filled with fluid and/or through which a fluid may flow, the temperature of which ensures a desired temperature of the specimen receptacle block 8.

In the shown embodiment of the base 4, a receiving means 102 is formed therein into which an electrically heated device 104, for example a so-called heating cartridge, may be inserted. By controlling the temperature of the device 104, the base 4 and, in particular, the regions thereof contacting the specimen receptacle block 8 may be controlled with respect to temperature such that specimen receptacle block 8 reaches a desired temperature. As a heating device, for example, a heating plate may be used.

Thermal control provided by the base 4 may also have an effect on the gassing head 12. For this purpose, for example, the regions of the gassing head 12 and the specimen receptacle block 8 contacting each other may be heat conducting.

The gassing system 2 may further comprise the following not shown components as system components: A device by means of which fluid, for example, nutrient medium for cell cultures, may be introduced into the fluid ducts 16; one or a plurality of devices for generating vacuum in the vacuum chambers 86; also means, for example, hoses, couplings, rigid lines and the like, for connecting the said devices may be included. The same applies to components for controlling the same.

The latter may also be included in the control means 14. In simple terms, the control means 14 is provided for an embodiment in which the control means 14 serves the purpose of controlling the heat generating device 104. Apart from input means (buttons, sliders, keyboards, etc.), the control means 14 may comprise indicators showing the current temperatures of the base 4, the heat emitting device 104, the specimen receptacle block 8 and/or the gassing head 12.

For supplying the gassing medium conducting ducts 72 and thus the specimen receptacles 26 with gassing medium, a mixing device 106 illustrated, in particular, in FIGS. 13 and 14 may be used. In the shown embodiments, the mixing device 106 comprises an identical number of first fluid outlets 108 and first fluid inlets 110 for each inlet port 76 of the gassing medium conducting ducts 72. Starting from the first fluid inlets 110, the fluid ducts 112 extend up to a mixing region 114. Fluid ducts 116 and optional fluid ducts 118 open into the mixing region 114, which ducts are, on the other hand, connected to second fluid inlets 120 and optional third fluid inlets 122. Starting from the mixing region 114, respective fluid ducts 124 extend towards the corresponding first fluid outlets 108.

The first fluid inlets 110 are each adapted for connection to a source (not shown) of a fluid intended to be a component of a contemplated gassing medium which may be output via the corresponding first fluid outlet 108. One or a number of comparable fluid sources may be used for all first fluid inlets 110 or different fluid sources may be used for at least two first fluid inlets 110.

Also the second fluid inlets 120 are each adapted for connection to a source (not shown) of a different fluid intended to be a component of the contemplated gassing medium which may be output via the corresponding first fluid outlet 108. One or a number of comparable fluid sources may be used for all second fluid inlets 120 or different fluid sources may be used for at least two second fluid inlets 120. Supplying different fluids to the mixing region enables generation of fluid mixture(s) which may be output as the gassing medium via the first fluid outlets 108.

Fluids conducted to the corresponding mixing region 114 via the fluid ducts 112 and 116 may be mixed therein for obtaining a fluid which is to be supplied to the specimen receptacles 26 as the gassing medium. A further fluid may be supplied to the mixing region via the optional third fluid inlets 122; the third fluid inlets 122 are, in particular, adapted for supplying a fluid differing from the fluid which may be supplied via the second fluid inlets 120. Thus, for example, air may be introduced for further dilution via the third fluid inlets 122.

Gassing medium (e.g. a fluid of one type, a mixture of two or more fluids) to be supplied to the gassing apparatus is provided by the mixing region 114 via the fluid ducts 124 and the first fluid outlets 108.

The specimen receptacles 26 may each be adapted, as explained above, for receiving an individual specimen container. Possible designs of specimen containers, which may be used as individual, separate specimen containers or as an insert comprising integral specimen containers, are described with reference to FIG. 15. A specimen container 130 comprises a bottom 132 and side walls 134. The interior space defined by the bottom 132 and the side walls 134 may have a circular cross-section in parallel with the bottom 132. A specimen to be gassed may be arranged directly, e.g. at the bottom, in this interior space.

The specimen to be gassed together with a fluid 134 (e.g. nutrient solution) may be disposed in the specimen container. In such cases, the specimen to be gassed may (in part) be immersed into the fluid 134, may just contact the same or may be arranged separately therefrom. Fluid 134 may be supplied and/or removed, for example, via the fluid ducts 16.

Furthermore, a membrane 136, e.g. a micro-porous membrane, may be used on which specimens, for example cells, to be examined may be arranged. The membrane 136—if present—may (in part) be immersed into the medium 134, may just contact the same or may be arranged separately therefrom. The micro-porous membrane 136 may be arranged, for example, by means of a specimen container insert 138. Specimens, for example cells, to be examined may be arranged on the membrane 136.

Operation of the embodiments described above may be as follows:

In the following, it will be referred, in a simplified manner, to a gassing apparatus or a gassing system comprising a gassing apparatus. The following explanations apply accordingly when using a number of gassing apparatuses.

Specimens to be gassed are introduced into individual, a plurality or all specimen receptacles 26 of the specimen receptacle block 8. Possible specimens include cell cultures, cell samples, tissue samples, bacteria, fungi and the like. Gassing media conceivable for gassing include gaseous media, for example, in form of pure gas or gases, gas mixtures, aerosols, atomized liquids, gases or gas mixtures including liquid droplets, suspended particles, solid particles, gaseous suspensions, atomized suspensions, etc. Gassing medium may be provided, for example, by a so-called smoking robot, by means of which cigarette smoke may be obtained, comparable to smoking a cigarette, in a technical manner. Furthermore, so-called aerosol generators and/or particle compressors may serve as gassing medium sources which are capable of concentrating (environmental) atmospheres.

The specimen receptacles 26 may be equipped with specimens, for example, in a specific environment (e.g. clean room environment). This is facilitated by using a gassing apparatus according to the invention. Said apparatus may be separately introduced into such an environment. Components which are required in the gassing process (only), such as for example devices providing gassing media, control means, supports, etc., do not have to be moved along with it.

After the specimens have been arranged in the specimen receptacles 26, the specimen receptacle block 8 and the gassing head 12 are secured to each other. The gassing apparatus is then arranged on the base 4 which may be located, for example, in another room. Therein, the supply and discharge lines, fluid ports, vacuum ports, etc. of the gassing device are connected. Depending on the design, individual, a plurality or all specimen containers 26 may be supplied with fluid, for example, via the fluid ducts 16. It is possible to detect or monitor the current fluid level in the specimen receptacle 26 by means of the respective level detecting means for each specimen receptacle. Information on fluid levels in receptacles 26 may be used for controlling the supply and/or discharge of fluid to or from individual, a plurality or all specimen receptacles 26.

The supply of fluid which may be controlled with respect to individual, a plurality or all gassing medium outlets 82 may be achieved by two measures which may be performed alternatively or collectively with respect to a gassing medium outlet 82. Controlling the gassing medium for a gassing medium outlet 82 may be achieved by controlling the gassing medium supplied to the respective gassing medium outlet 82. For this purpose, the gassing amount supplied to a corresponding gassing medium duct 72 may be controlled, for example, upstream of the inlet port 76. The amount of gassing medium available may be controlled by a closing member arranged between the gassing medium ducts 72 and the open lower end of the gassing medium outlet 82; the closing member, for example, in form of a valve, may be arranged in or at the gassing medium outlet 82.

A further approach of controlling the gassing medium may be achieved via the vacuum chambers 88. If vacuum is applied to the corresponding vacuum port 92, vacuum is generated in the associated specimen receptacle 26 via the vacuum chamber 88 and the at least one aperture 90 thereof. This vacuum acts on the gassing medium via the lower open end of the respective gassing medium outlet 82. The gassing medium is transported into the specimen receptacle 26 by means of this vacuum and may then be used for gassing a specimen therein.

A modular structure of fumigation or gassing systems and apparatuses is disclosed. The separable design of the gassing or fumigation apparatuses within the overall system enables execution of the respective individual working and operation steps at different sites/locations. The gassing or fumigation systems may be used in succession with individual or a plurality, even different, gassing or fumigation apparatuses wherein, incidentally, the same components may still be used without modification. This applies, in particular, to fluid and gassing medium supply lines, ports and the like. Also the base and control components may be retained. Gassing or fumigation apparatuses having a different number of specimen receptacles may be used in the overall system without further modification. The structures, in particular, of the specimen receptacle block, due to their, in part, one-piece design, are easy to manufacture automatically, robust and easy to handle. In particular with respect to experimental laboratory applications, arrangements comprising complex interconnections having, in part, numerous components made of fragile materials (e.g. glass) are avoided.

The invention claimed is:

1. A gassing apparatus comprising:
    a one-piece specimen receptacle block including at least two specimen receptacles formed therein and a fluid supply duct formed therein below the specimen receptacles for supplying fluid to the specimen receptacles,
    a gassing head for supplying gassing medium to the specimen receptacles, said gassing head is disposed above and connected to the specimen receptacle block and said gassing head comprises an inlet and an outlet with a gassing medium duct extending therebetween, the gassing medium duct being connected to a plurality of gassing medium outlets, each gassing medium outlet extending downward into one of the specimen receptacles for conducting gassing medium downward to the said specimen receptacle, and
    the gassing head further including a vacuum duct in communication with at least one vacuum chamber in communication with each of the specimen receptacles and disposed above the gassing medium outlets for drawing gassing medium downward through the gassing medium outlets and upward through the specimen receptacles.

2. The gassing apparatus according to claim 1, wherein the fluid supply duct is formed separately in the specimen receptacle block for separate supply of at least two of the at least two specimen receptacles.

3. The gassing apparatus according to claim 1, wherein the gassing medium duct is formed separately in the gassing head for separate supply of at least two of the gassing medium outlets.

4. The gassing apparatus according to claim 1, wherein at least two of the at least two specimen receptacles are each associated with a level detecting means.

5. The gassing apparatus according to claim 1, wherein an individual level indicator is provided for at least one of the at least two specimen receptacles at an outer surface of the specimen receptacle block.

6. The gassing apparatus according to claim 1, comprising a device for separately supplying each of the at least two specimen receptacles with gassing medium independently of a supply of gassing medium to other specimen receptacles.

7. The gassing apparatus according to claim 1, wherein the apparatus comprises separate vacuum chambers, each of which are associated with a one of the gassing medium outlets.

8. The gassing apparatus according to claim 7, wherein the each of the at least two specimen receptacles each include an aperture the provides communication between each specimen receptacles and it associated gassing medium outlet to its corresponding vacuum chamber.

9. The gassing apparatus according to claim 1, comprising a seal adapted for arrangement on an upper surface of the specimen receptacle block.

10. The gassing apparatus according to claim 9, wherein the seal comprises apertures through which the specimen receptacles may be introduced, at least in part, into the specimen receptacles.

11. The gassing apparatus according to claim 1, further comprising, for each vacuum chamber, a device for individual vacuum control being adapted to separately and independently supply gassing medium to the associated specimen receptacle.

12. A gassing system comprising
    at least one gassing apparatus according to claim 1, and
    a base.

13. The gassing system according to claim 12, further comprising a device for mixing gassing media and supplying a desired gassing medium to the specimen receptacles.

14. A gassing apparatus comprising:
    a one-piece specimen receptacle block including at least two specimen receptacles formed therein and a fluid supply duct formed therein below the specimen receptacles for supplying fluid to the specimen receptacles, and
    a gassing head for supplying gassing medium to the specimen receptacles, said gassing head is disposed above and connected to the specimen receptacle block and said gassing head comprises an inlet and an outlet with a gassing medium duct extending therebetween, the gassing medium duct being connected to a plurality of gassing medium outlets, each gassing medium outlet extending downward into one of the specimen receptacles for conducting gassing medium from the gassing medium duct downward to each of the specimen receptacles, and
    the gassing head further including a vacuum duct in communication with at least two vacuum chambers, each vacuum chamber being in communication one of the specimen receptacles above the respective gassing medium outlet that extends downward into said specimen receptacle for drawing gassing medium downward through the gassing medium outlets and upward through the respective specimen receptacles.

* * * * *